(12) United States Patent
Morsi

(10) Patent No.: US 8,292,914 B2
(45) Date of Patent: Oct. 23, 2012

(54) ANEURYSM FLOW BARRIER

(75) Inventor: Hesham Morsi, Houston, TX (US)

(73) Assignee: Noha LLC, Houston, TX (US)

( * ) Notice: Subject to any disclaimer, the term of this patent is extended or adjusted under 35 U.S.C. 154(b) by 0 days.

(21) Appl. No.: 13/182,497

(22) Filed: Jul. 14, 2011

(65) Prior Publication Data

US 2012/0046676 A1  Feb. 23, 2012

Related U.S. Application Data

(60) Continuation of application No. 12/434,137, filed on May 1, 2009, now Pat. No. 7,993,364, which is a continuation of application No. 11/039,908, filed on Jan. 24, 2005, now abandoned, which is a division of application No. 09/925,433, filed on Aug. 10, 2001, now Pat. No. 6,855,154.

(60) Provisional application No. 60/224,361, filed on Aug. 11, 2000.

(51) Int. Cl.
*A61M 29/00* (2006.01)
(52) U.S. Cl. ...................................... 606/200; 604/96.01
(58) Field of Classification Search .................. 606/158, 606/192, 194, 200; 623/23.72, 23.74; 604/96.01
See application file for complete search history.

(56) References Cited

U.S. PATENT DOCUMENTS

| | | |
|---|---|---|
| 4,311,146 A | 1/1982 | Wonder |
| 4,341,218 A | 7/1982 | Ü |
| 4,360,023 A | 11/1982 | Sugita et al. |
| 4,364,392 A | 12/1982 | Strother et al. |
| 4,395,806 A | 8/1983 | Wonder et al. |
| 4,484,581 A | 11/1984 | Martin et al. |
| 4,658,822 A | 4/1987 | Kees |
| 4,660,558 A | 4/1987 | Kees, Jr. |
| 4,710,192 A * | 12/1987 | Liotta et al. ................... 606/108 |
| 4,765,335 A | 8/1988 | Schmidt |
| 4,932,955 A | 6/1990 | Merz et al. |
| 4,966,603 A | 10/1990 | Focelle et al. |
| 5,122,136 A | 6/1992 | Guglielmi et al. |
| 5,411,549 A | 5/1995 | Peters |
| 5,423,829 A | 6/1995 | Pham et al. |
| 5,522,823 A | 6/1996 | Kuntz et al. |

(Continued)

FOREIGN PATENT DOCUMENTS

JP  1-249045  10/1989

(Continued)

OTHER PUBLICATIONS

Micrus Corporation, "Micrus Microcoil Delivery System", 2001, Micrus Corporation, http://www.micruscorp.com/coils.html, Feb. 15, 2002, p. 1 of 2.

(Continued)

*Primary Examiner* — Victor Nguyen
(74) *Attorney, Agent, or Firm* — Fulbright & Jaworski LLP

(57) ABSTRACT

A collapsing clip including a plurality of collapsed self expanding wire frame segments is contained within the distal end of a catheter. The clip can be delivered to the neck of an aneurysm within the neurovascular system using a catheter. The collapsing clip impinges the distal and proximal framed wire segments onto the neck of the aneurysm. The framed wire segments are inter positioned so that the diamond shaped spaces between the wires are substantially blocked. The neck of the aneurysm is blocked by the distal and proximal framed wire segments forming a barrier.

14 Claims, 11 Drawing Sheets

U.S. PATENT DOCUMENTS

| | | |
|---|---|---|
| 5,522,836 A | 6/1996 | Palermo |
| 5,540,680 A | 7/1996 | Guglielmi et al. |
| 5,624,449 A | 4/1997 | Pham et al. |
| 5,634,932 A | 6/1997 | Schmidt |
| 5,702,418 A | 12/1997 | Ravenscroft |
| 5,733,294 A * | 3/1998 | Forber et al. .................. 606/151 |
| 5,749,894 A | 5/1998 | Engelson |
| 5,758,420 A | 6/1998 | Schmidt et al. |
| 5,769,816 A | 6/1998 | Barbut et al. |
| 5,776,097 A | 7/1998 | Massoud |
| 5,795,331 A | 8/1998 | Cragg et al. |
| 5,824,059 A | 10/1998 | Wijay |
| 5,855,578 A | 1/1999 | Guglielmi et al. |
| 5,868,783 A | 2/1999 | Tower |
| 5,891,128 A | 4/1999 | Gia et al. |
| 5,895,385 A | 4/1999 | Guglielmi et al. |
| 5,919,187 A | 7/1999 | Guglielmi et al. |
| 5,921,957 A | 7/1999 | Killion et al. |
| 5,925,016 A | 7/1999 | Chornenky et al. |
| 5,925,037 A | 7/1999 | Guglielmi et al. |
| 5,928,226 A | 7/1999 | Guglielmi et al. |
| 5,928,260 A | 7/1999 | Chin et al. |
| 5,935,148 A | 8/1999 | Villar et al. |
| 5,941,888 A | 8/1999 | Wallace et al. |
| 5,941,896 A | 8/1999 | Kerr |
| 5,944,714 A | 8/1999 | Guglielmi et al. |
| 5,947,962 A | 9/1999 | Guglielmi et al. |
| 5,947,963 A | 9/1999 | Guglielmi |
| 5,976,126 A | 11/1999 | Guglielmi |
| 5,976,162 A | 11/1999 | Doan et al. |
| 5,984,929 A | 11/1999 | Bashiri et al. |
| 6,010,498 A | 1/2000 | Guglielmi |
| 6,015,424 A | 1/2000 | Rosenbluth et al. |
| 6,017,977 A | 1/2000 | Evans et al. |
| 6,024,754 A | 2/2000 | Engelson |
| 6,048,333 A | 4/2000 | Lennox et al. |
| 6,051,607 A | 4/2000 | Greff |
| 6,053,941 A | 4/2000 | Lindenberg et al. |
| 6,059,779 A | 5/2000 | Mills |
| 6,066,133 A | 5/2000 | Guglielmi et al. |
| 6,077,260 A | 6/2000 | Wheelock et al. |
| 6,083,220 A | 7/2000 | Guglielmi et al. |
| 6,096,021 A | 8/2000 | Helm et al. |
| 6,123,714 A | 9/2000 | Gia et al. |
| 6,146,396 A | 11/2000 | Konya et al. |
| 6,258,115 B1 | 7/2001 | Dubrul |
| 6,454,780 B1 | 9/2002 | Wallace |
| 6,585,748 B1 | 7/2003 | Jeffree |
| 2002/0010481 A1 | 1/2002 | Jayaraman |
| 2003/0028209 A1 | 2/2003 | Teoh et al. |

FOREIGN PATENT DOCUMENTS

| | | |
|---|---|---|
| JP | 2/154748 | 6/1990 |
| JP | 3-60652 | 3/1991 |
| JP | 9-70405 | 3/1997 |
| WO | WO-97/04813 | 2/1997 |
| WO | WO-97/27888 | 8/1997 |
| WO | WO-97/45131 | 12/1997 |
| WO | WO-98/09570 | 3/1998 |

OTHER PUBLICATIONS

Company News on Call, "NMT Medic. Announces Agreement to Sell Vena Cava Filter Assts", http://www.prnewswire.com, Feb. 15, 2002, p. 1 of 2.

ORCMT, Success Story, "Clinical Neuro Systems", http://orcmt.oakridge.org/success/clinical.html, Feb. 15, 2002, p. 1 of 2.

Mizuho, "Sugita Aneurysm Clips", http://www.mizuho.com/aclips1.html, Feb. 15, 2002, p. 1 of 1.

Untitled Stacked Page, Press Releases, Aug. 2001: MicroVention Raises $12.5 Million in Late-Stage Financing: Minimally Invasive Technology Attracts Several New Medical Device Investors, http://www.microvent.com, Feb. 15, 2002, p. 1 of 2.

Onyx™ Liquid Embolic System, http://www.microtherapeutics.com/products_onyx.html, Feb. 15, 2002, p. 1 of 3.

K.I. Arnautovic, et al., "A Combined Microsurgical Skull-Base and Endovascular Approach to Giant and Large Paraclinoid Aneurysms", Elsevier Science, Inc., 1998, pp. 504-516.

Yiu-Wah Fan, et al., "Retrograde Suction Decompression of Paraclinoid Aneurysm—Revised Technique", Elsevier Science, Inc., 1999, pp. 129-131.

T. Schmitz-Rode, et al. Embolotherapy of Aneurysms Under Temporary Balloon Occlusion of the Neck, Investigative Radiology, 1999, pp. 317-321.

Puay-Yong Ng, et al., "Intraoperative Endovascular Treatment as an Adjunct to Microsurgical Clipping of Paraclinoid Aneurysms", J. Neurosurg., vol. 93, Oct. 2000, pp. 554-559.

* cited by examiner

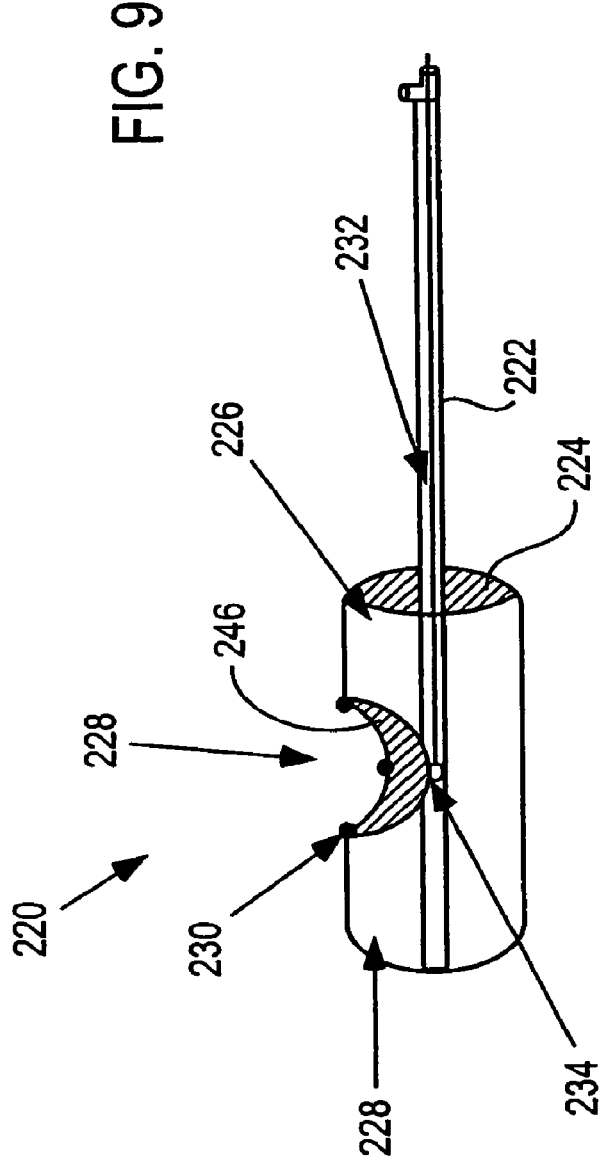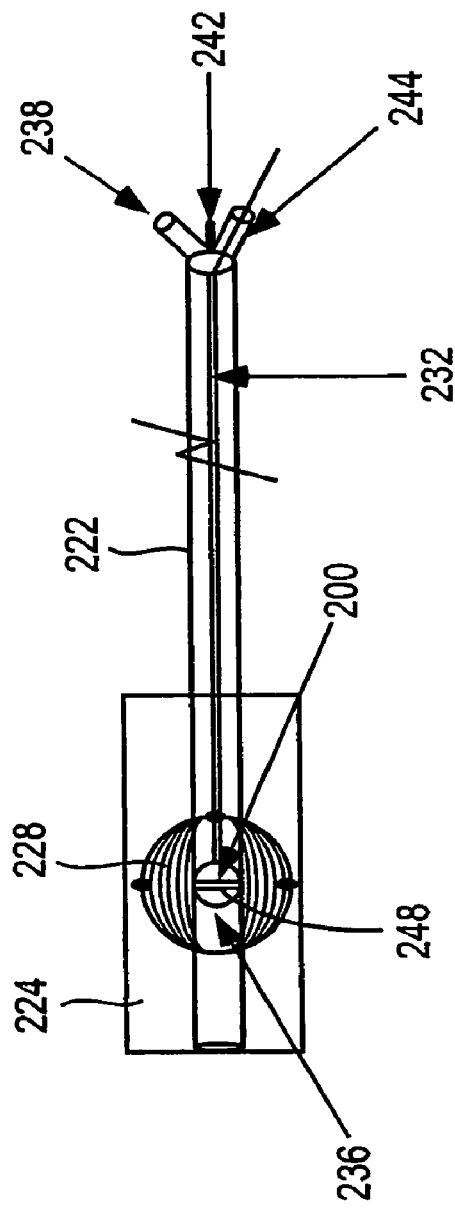

ANEURYSM FLOW BARRIER

CROSS-REFERENCE TO RELATED APPLICATIONS

This application is a continuation of U.S. patent application Ser. No. 12/434,137, filed on May 1, 2009, now U.S. Pat. No. 7,993,364, which is a continuation of U.S. patent application Ser. No. 11/039,908 filed on Jan. 24, 2005, now abandoned, which was a divisional of U.S. patent application Ser. No. 09/925,433, filed on Aug. 10, 2001, now U.S. Pat. No. 6,855,154, which claims priority to U.S. Provisional Patent Application No. 60/224,361, filed Aug. 11, 2000. The entire disclosures of these prior applications are incorporated herein by reference.

TECHNICAL FIELD

The present invention relates to systems and processes for treating an aneurysm, and more particular to an endovascular system and process for collapsing an aneurysm.

BACKGROUND OF THE INVENTION

Aneurysm treatments have been proposed using a wide variety of processes and devices, which have enjoyed various levels of success and acceptance. Such systems and processes include aneurysm clips, intravascular coils, intravascular injections, detachable intravascular balloons, and the like.

These prior devices, however, have proven to be difficult to employ, oftentimes do not lend themselves to deployment in all sizes of aneurysms, can be imprecise in their deployment, their installation can be very time consuming, risk rupture of the aneurysm because they increase its size, can risk recanalization and/or migration of the device in the patient's vasculature, and may not treat the mass effect that the aneurysm may have caused. Furthermore, the presence of adhesions in the aneurysm makes it difficult to collapse the aneurysm. There therefore remains an unmet need in the art for systems and processes which do not suffer from one or more of these deficiencies.

SUMMARY OF THE INVENTION

According to a first aspect of the invention, a method of treating an aneurysm in a patient comprises the steps of advancing a compressed clip through the distal end of a catheter and into the aneurysm, expanding portions of the clip inside the aneurysm, and folding a distal segment of the clip on itself together with the adjacent wall of the aneurysm as it becomes dislodged from the stretching bar.

According to a second aspect of the invention, a system useful for treating an aneurysm in a blood vessel of a mammalian patient, the aneurysm having a neck, a wall, and a cavity, comprises an elongated shaft having a proximal end, a distal end, a longitudinal direction defined between the proximal end and the distal end, and including at least one lumen extending therethrough, and a self-expanding frame positioned at the distal end of the shaft, the frame including a plurality of self-expanding sections and at least one joint, each of the plurality of self-expanding sections having an unbiased, expanded condition and a biased, collapsed condition, each of the plurality of self-expanding sections being foldable about one of the at least one joint when in a biased, collapsed condition.

According to a third aspect of the invention, a catheter useful for accessing a vascular location adjacent to an aneurysm, comprises a hollow shaft including a proximal end, a distal end, a longitudinal direction defined between the proximal end and the distal end, a port in a distal portion of the shaft, and including at least one lumen extending therethrough. and an inflatable member mounted on the shaft adjacent to the shaft distal end, the inflatable member in fluid communication with the shaft at least one lumen, the inflatable member including a proximal end, a distal end, and a wall between the proximal end and the distal end which extends to the shaft so that the shaft port is directly exposed to the exterior of the balloon, the wall delimiting a central working channel.

According to a fourth aspect of the invention, a method of treating an aneurysm in a patient comprises the steps of advancing a compressed clip through the distal end of a catheter and into the aneurysm, expanding portions of the clip inside the aneurysm, and folding a distal segment of the clip on itself together with the adjacent wall of the aneurysm as it becomes dislodged from the stretching bar.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which:

FIG. 9 illustrates a side elevational view of a catheter in accordance with the present invention;

FIG. 10 illustrates a top plan view of the catheter of FIG. 9;

DESCRIPTION OF THE PREFERRED EMBODIMENTS

Figure 1:
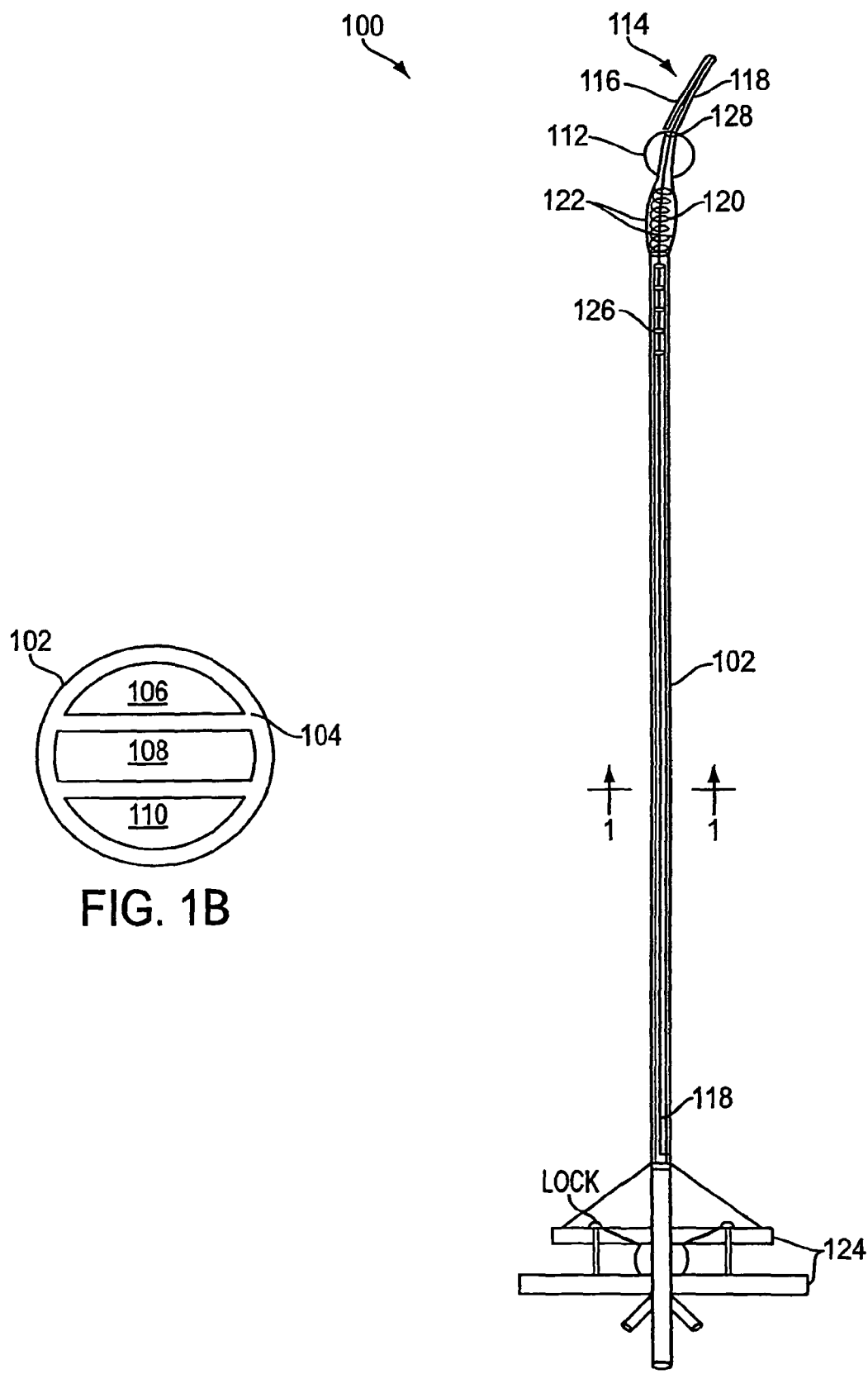
FIGS. 1a and 1b illustrates longitudinal and cross-sectional views of an exemplary embodiment of an apparatus in accordance with the present invention.

Apparatus and methods in accordance with the present invention have numerous advantages over prior aneurysm clips and methods. Among these advantages, immediate closure of an aneurysm can be achieved with a relatively easy-to-use method. The apparatus and methods can be used to treat all aneurysms regardless of the size or the neck width, and can achieve precise locational deployment and decreased procedure time. The risk of rupture can be decreased, since the aneurysm volume is never increased. Additionally, occlusion of the aneurysm neck can be achieved by a balloon in case rupture does occur. Decreased risk of distal embolization, little or no risk of recanalization or migration, strengthening of the arterial wall at the site of the aneurysm, good visualization of the device during and after deployment, and immediate elimination of any mass effect the aneurysm may have caused can also be achieved.

Referring to the drawing figures, like reference numerals designate identical or corresponding elements throughout the several figures.

FIGS. 1a and 1b illustrate a first exemplary embodiment of a system in accordance with the present invention. The system 100 includes a triple lumen catheter 102 having a sidewall 104 and three lumenae 106, 108, 110 extending longitudinally therethrough. An inflatable member 112, such as a balloon. is positioned adjacent a distal end 114 of the catheter, and is in fluid communication with one of the three lumenae, e.g., lumen 106. A collapsible element or clip 116 is removably mounted to the distal end of the catheter and is movable between a retracted and collapsed condition, illustrated in FIG. 1a, and an extended and expanded condition, illustrated in FIGS. 4a, 4b, 5a, and 5b. In order to effect collapse and expansion of the clip 116, a longitudinally movable stretching bar 118 extends proximally from the distal end of the catheter, and preferably extends both within the clip 116 and the one of the catheter lumenae, e.g., lumen 108.

The system 100 also preferably includes a flexible portion in the distal end of the catheter 102 so that the catheter can more easily navigate the sometimes tortuous paths encountered during endovascular procedures. By way of example and not of limitation, a spring 120 can be incorporated into the distal portions of the catheter 102, preferably proximal of the balloon 112, to permit the catheter to more easily flex and bend. A pair of steering wires 122 are attached to the catheter distal to the flexible portion 120 and to a steering mechanism or station 124 at the proximal end of the catheter. Steering mechanisms for catheters have previously been proposed in the patent literature, and therefore a detailed description of station 124 will be omitted herein.

The catheter 102 also preferably includes at least one, and more preferably, several distal side perfusion holes 126 which are in fluid communication with one of the three lumenae, e.g., lumen 110. The catheter also includes a one way valve 128 positioned distally of the balloon 112 and also in fluid communication with one of the lumenae. Valve 128 is oriented to permit a vacuum drawn in the catheter to suction through the valve, for purposes which will be explained in greater detail below. In accordance with one preferred embodiment, both the side holes 126 and the valve 128 are in fluid communication with the same lumen; because the one way valve 128 only permits flow into the catheter through the valve, perfusion of fluid, e.g. contrast agent, through the side holes 126 will not exit out the catheter through the valve.

Figure 5A:
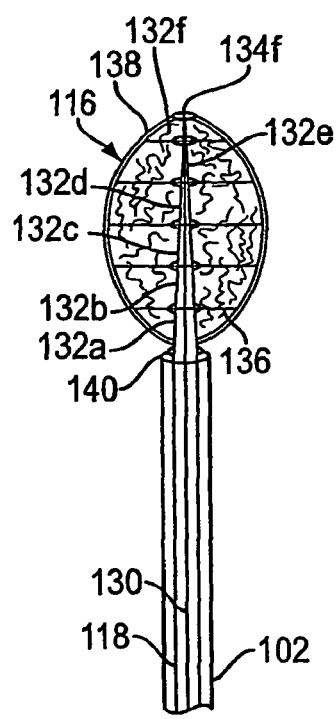
FIGS. 5a and 5b illustrate two embodiments of apparatus in accordance with the present invention.
Figure 5B:
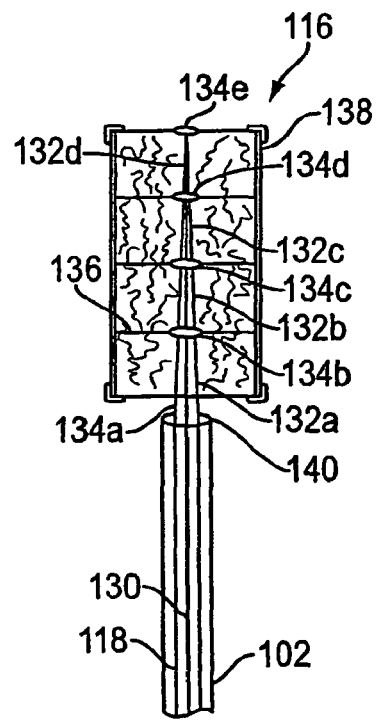

Turning briefly to FIGS. 5a, 5b, and 6a-6c, further details of clips in accordance with the present invention are illustrated. In general, clips in accordance with the present invention are releasable from the catheter or other deployment device inside an aneurysm. The clips also have a collapsed condition into which the clips are biased by their own structures, and an expanded condition into which the clips must be moved. FIGS. 5a and 5b illustrate two different versions of a clip 116 in an expanded condition, with the stretching bar 118 extending through the catheter 102 and through the clip 116. As illustrated in FIGS. 5a and 5b, the stretching bar 118 also includes a thread, wire, or the like 130 which is connected to the distal most end of the stretching bar and extends proximally through the catheter 102, preferably within the stretching bar itself.

The stretching bar 118 includes at least one, and preferably several telescoping sections 132a-f of decreasing outer diameter. Thus, section f can slide into section e, section e into section d, and so forth, when the wire 130 is pulled proximally. The clip 116 includes at least one, and preferably several rings 134a-f which are releasably held on the outer surface of the stretching bar 118, e.g., by a friction fit, a frangible coupling, or the like. To each ring 134 a set of arms 136 are attached so that the arms can articulate and fold in toward the stretching bar, in a manner somewhat similar to an umbrella. An outer trellis or covering 138 extends between the opposite ends of the arms.

Figure 2:
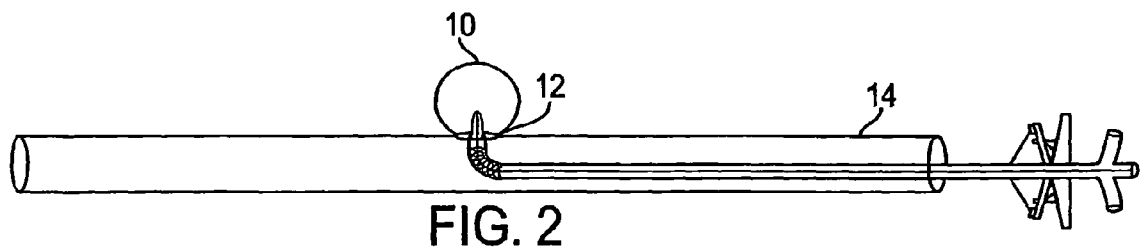
FIG. 2 illustrates the apparatus of FIG. 1 in use according to an exemplary method.
Figure 6C:
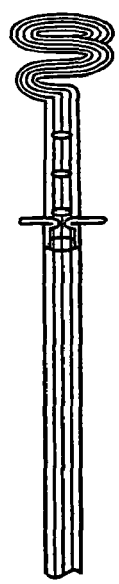
FIGS. 6a-6c illustrate successive steps of use of an apparatus in accordance with the present invention.
Figure 6B:
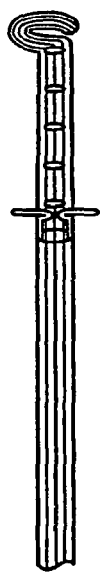
Figure 6A:
Figure 7:
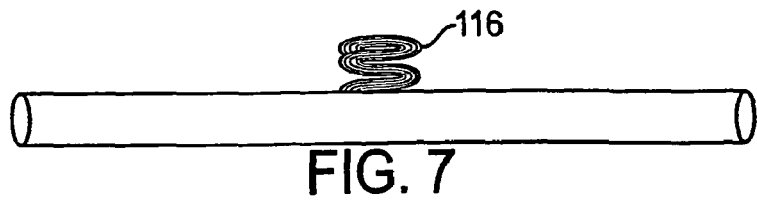
FIG. 7 illustrates a vascular aneurysm after collapse thereof in accordance with the present invention.

In order to deploy the clip 116, the distal end of the catheter 102 is positioned in the neck of an aneurysm, as illustrated in FIG. 2. The stretching bar, which is already in its own expanded condition, is pushed distally, carrying with it the collapsed clip 116. As the clip exits the distal end of the catheter, as through a distal port 140, successive sections of the clip expand outward until the clip is fully exposed and outside of the catheter. The wire 130 is then pulled proximally, causing the sections of the stretching bar to telescope into one another, with the distalmost section 132f moving proximally first into the next most distal section 132e. As the distalmost end of the section 132f moves into the distalmost end of the section 132e, the ring 134 which was received on the section 132f is pulled off of the stretching bar, leaving that distalmost section of the clip collapsed proximally against the adjacent section. The wire 130 is pulled proximally until each of the sections 132 has telescoped into the adjacent section, causing a collapsing cascade of the clip sections proximally. When the proximalmost section of the stretching bar has been retracted, the clip is left fully collapsed and separated from the stretching bar and the deployment device, e.g., catheter 102. FIGS. 6a-c illustrate successive views of this serial collapse of the clip from a side view, while FIG. 7 schematically illustrates the completely collapsed clip in situ.

According to additional embodiments, the releasable connections between the arms 136 and the stretching bar 118 can be formed as twist locks, meltable connections, for which a resistive heater is positioned at each arm and voltage source is connected thereto, or the like as will be readily appreciated by one of ordinary skill in the art.

Figure 8:
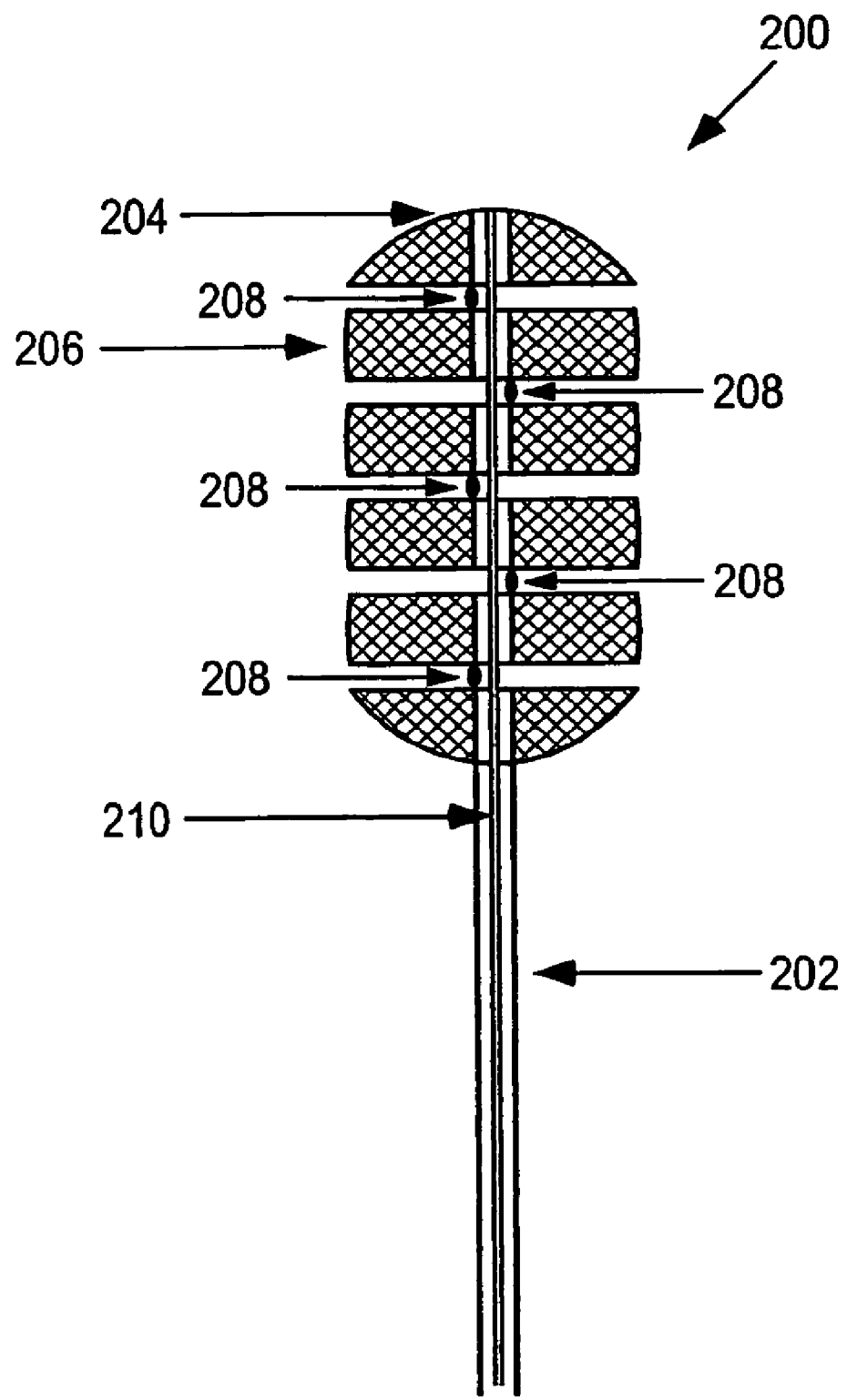
FIG. 8 illustrates a distal end of yet another embodiment of a device in accordance with the present invention.
Figure 11:
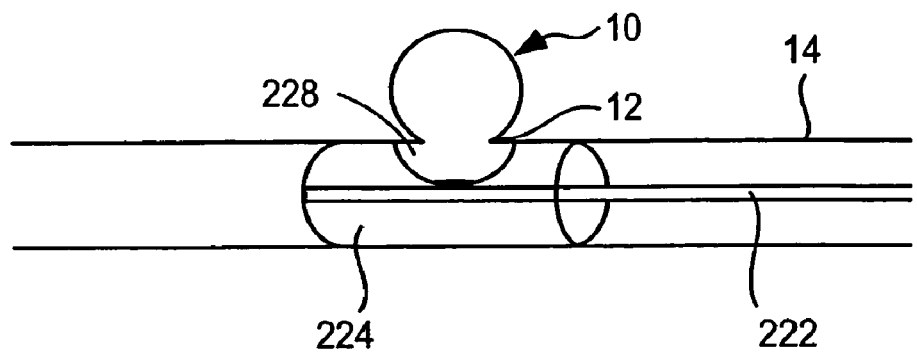
FIGS. 11-17 diagrammatically illustrate several steps of treating an aneurysm in accordance with an aspect of the present invention.
Figure 12:
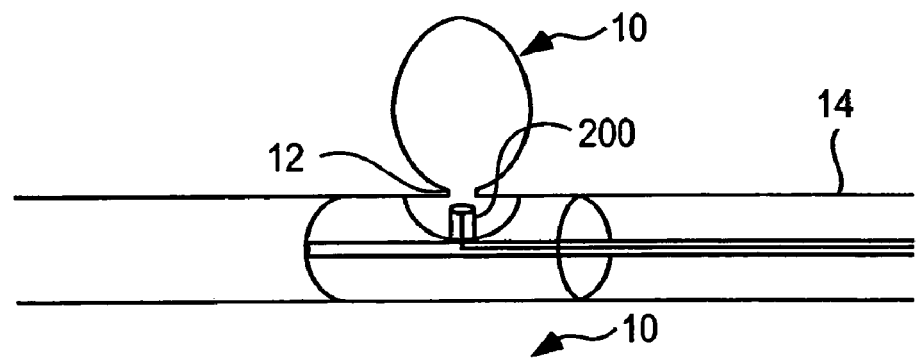
Figure 13:
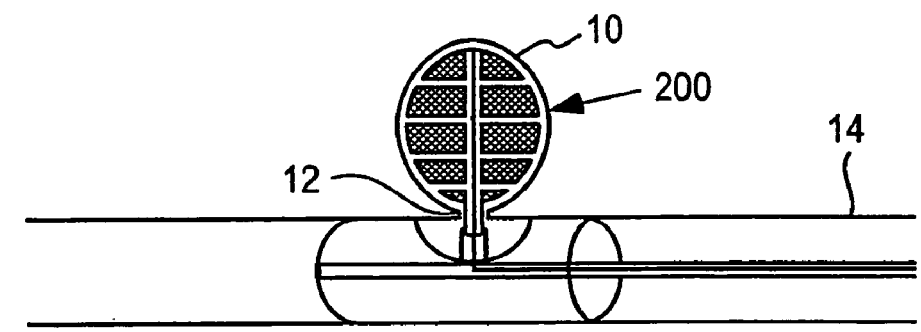
Figure 14:
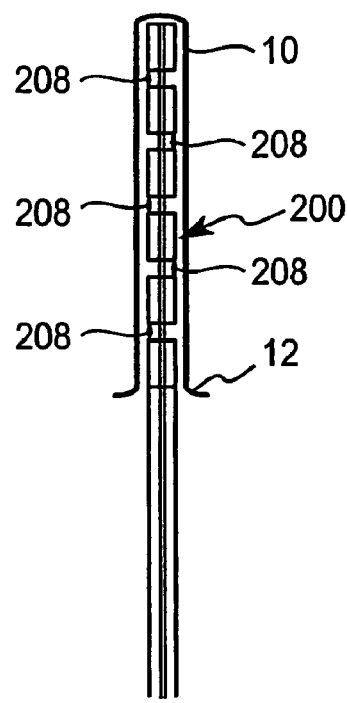
Figure 16:
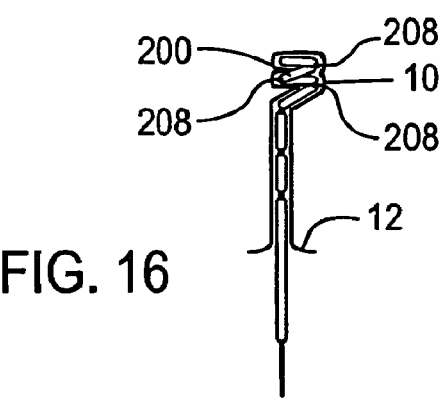
Figure 15:
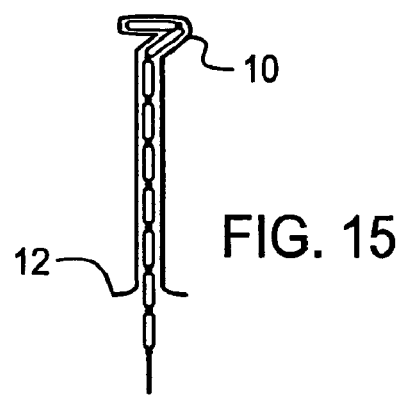
Figure 17:
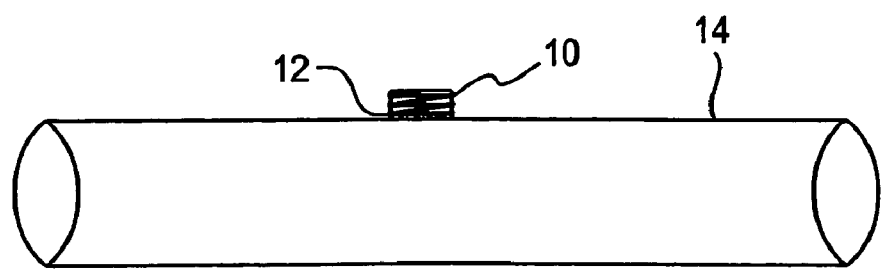
Figure 18:
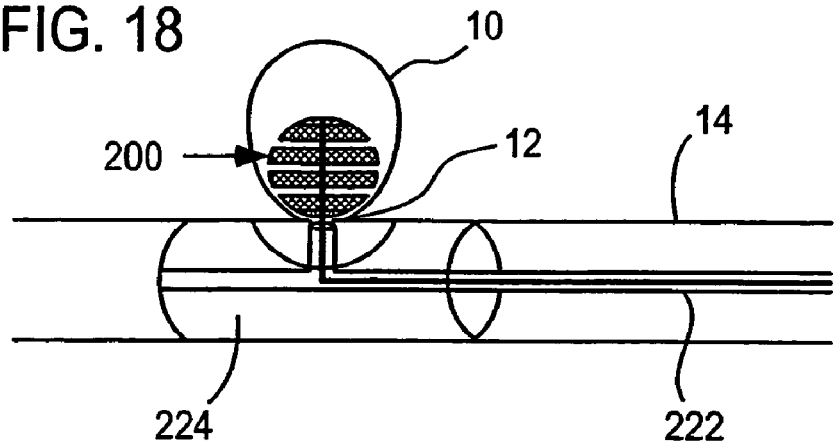
FIGS. 18-21 diagrammatically illustrate several steps of treating an aneurysm in accordance with another aspect of the present invention.
Figure 19:
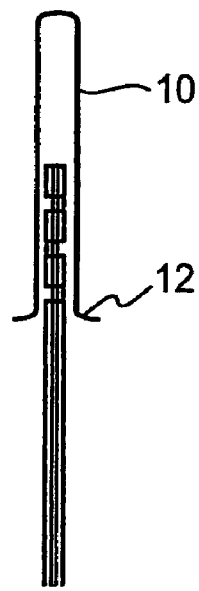
Figure 20:
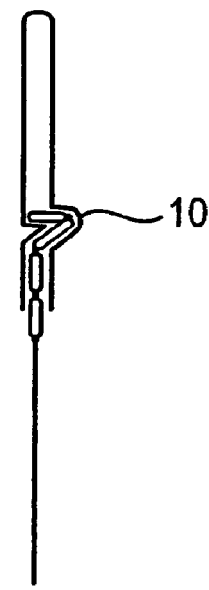
Figure 21:
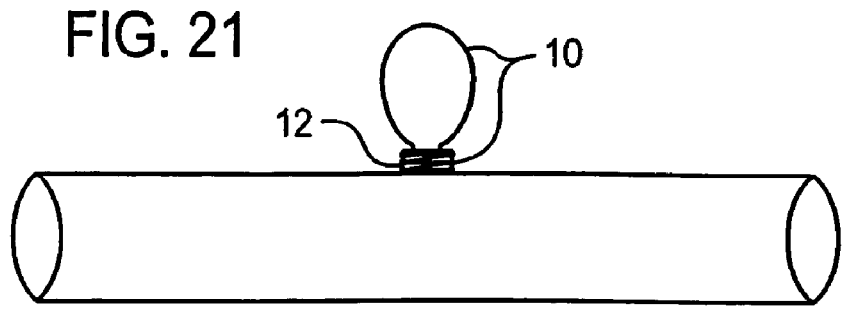

Turning now to FIG. 8, yet another embodiment of a clip in accordance with the present invention is illustrated. Clip 200 includes a longitudinally extending hollow, preferably cylindrical shaft 202 which extends to a closed, and optionally sealed, distal end 204. A self-expanding frame 206 is mounted about the distal portions of the shaft 202, and includes a number of segments which can fold about a number of collapsing joints 208. Preferably, the joints 208 are positioned in an alternating fashion on different sides of the clip 200, so that the clip can be folded up in an accordion-type manner. When each of the segments of the frame 206 fold about each joint 208, that segment folds onto an adjacent segment, as described in greater detail below. Each joint 208 includes a laterally extending leaf spring which has an unbiased, V-shaped orientation and a biased, flat orientation. Because of the presence of the spring in each joint 208, each segment is biased to fold upon itself, as illustrated in the drawing figures. A stiffening wire, stretching bar, or mandrel 210 extends through each of the segments of the frame, and prevents the springs of each of the joints 208 from folding each segment upon itself, as described in greater detail below.

The stiffening wire or stretching bar 210 extends longitudinally through the shaft 202. The wire or bar 210 allows the practitioner to straighten or laterally collapse the frame 206; that is, when the bar/wire/mandrel 210 is pushed distally against the distal end 204, the frame 206 can be stretched and collapsed, and proximal retraction removes this force on the frame and permits the frame to expand. Self-expanding frames are well known to those of skill in the art, such as those known for use in constructing vascular stents, and therefore the constructional details of frame 206 are omitted from this description for brevity's sake. As described in greater detail below, the self-expanding frame is constrained from expanding when advanced through the vasculature because the frame is carried in a catheter shaft which is sized to prevent the frame from expanded until the clip is moved out of the catheter. Such a practice is also known in the art of vascular stents, which are typically carried in a collapsed condition inside a carrier catheter, and thereafter pushed out of the catheter which permits them to expand.

Preferably, at least portions of the shaft 202 are configured so that upon rotation of the shaft about the longitudinal axis, the shaft is released from the frame 206. By way of example and not of limitation, distal portions of the shaft 202 can include a detent which will pass through correspondingly sized and shaped holes in the sections of the frame 206 only when the shaft is rotated to align the detent and hole. Other suitable mechanisms will be readily apparent to those of skill in the art.

FIGS. 9 and 10 illustrate side elevational and top plan views, respectively, of a catheter 220 which is useful for accessing and positioning a clip, such as clip 200, in an aneurysm 10. The catheter 220 includes a longitudinally extending shaft 222 dimensioned and formed of materials so that it can traverse the vasculature of the patient to be positioned immediately next to an aneurysm that the practitioner intends to treat. An inflatable balloon 224 is mounted on the distal end of the shaft 222, and includes proximal 226 and distal 228 inflatable portions. A central working channel 228 is formed in the balloon 224 by a portion 246 of the wall of the balloon extending inward to the shaft 222. Preferably, at least one, and more preferably several radiopaque markers 230 are located around the central working channel 228 so that its position in the patient can be monitored fluoroscopically.

The catheter 220 also preferably includes a mechanism or the like which directs a clip radially outward through the working channel 228 when the clip is pushed distally through the shaft 222. According to one exemplary embodiment, this mechanism can be a ramp shaped surface formed in the lumen of the shaft 222, so that when the clip is pushed distally through the shaft, the clip's distal motion is converted into radial motion out of the shaft and into the working channel. According to yet another exemplary embodiment, a deflectable tube 234 can be mounted on the shaft at the base of the working channel 228, and a steering thread 232 is attached to the tube 234. The steering thread extends proximally through the shaft 222 and exits the shaft or is otherwise made available to the practitioner to manipulate. Upon proximal pulling on the steering thread 232, the tube 236 can be deflected to point toward the central working channel 228, thus directing any clip, such as clip 200, which is pushed through the tube 234 into the working channel.

Several lumenae extend through the shaft 222. A suction lumen 236 extends from a distal port 248, located where the working channel 228 meets the shaft 222, to a proximal fitting or suction end 238, and includes a lock 242. The lock 242 is operable to seal the lumen 236 so that a relative vacuum can be maintained in the lumen. For example, lock 242 can be a stopcock valve. A proximal fitting 244 leads to another lumen of the shaft 222, and is the lumen which leads to the deflectable tube 234 and is the lumen in which the clip, e.g., clip 200, is longitudinally advanceable. Thus, the clip 200 can be loaded through the fitting 244 or the tube 234, into the shaft 222 with proximal portions of the clip extending proximally out of the fitting 244. In this orientation. the clip is in a collapsed condition because the internal dimensions of the lumen are selected to constrain the clip from self-expanding. Thereafter, the clip can be advanced distally, through the tube 234 and laterally into the working channel 228.

FIGS. 11-17 illustrate several steps in an exemplary method in accordance with the present invention which utilizes clip 200 and catheter 220, and are described in more detail below.

Figure 22:
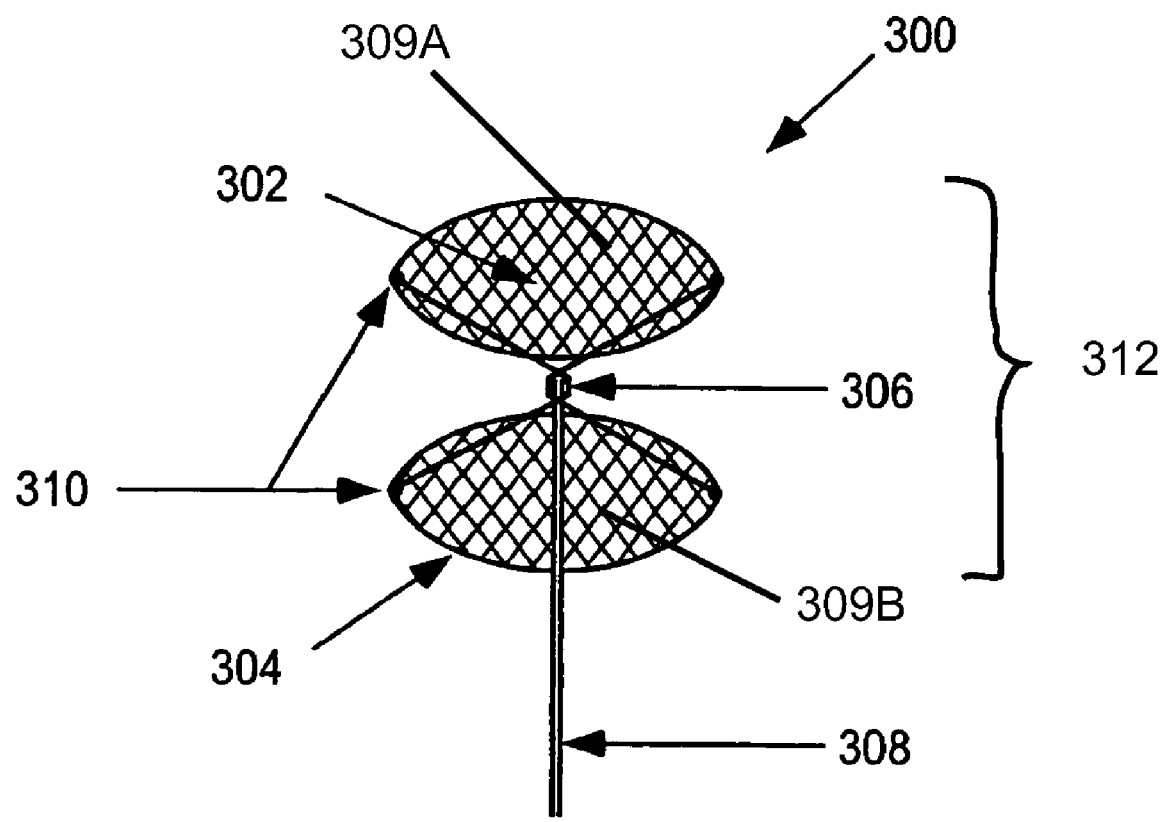
FIG. 22 illustrates a distal end of yet another embodiment of a device in accordance with the present invention.
Figure 23:
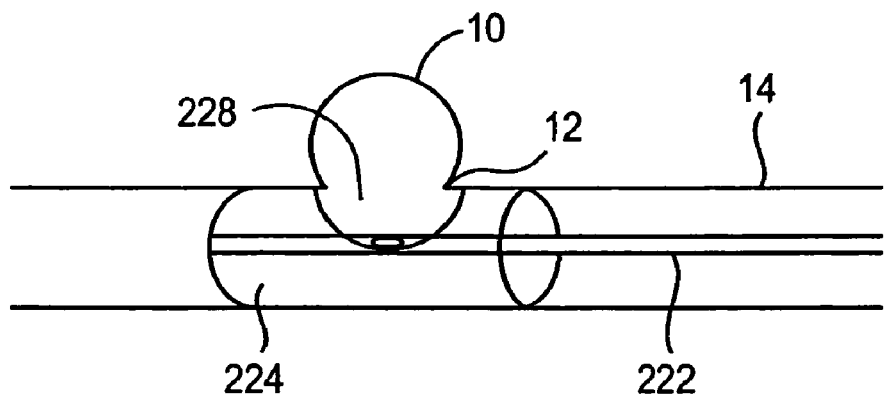
FIGS. 23-28 diagrammatically illustrate several steps of treating an aneurysm in accordance with yet another aspect of the present invention.
Figure 24:
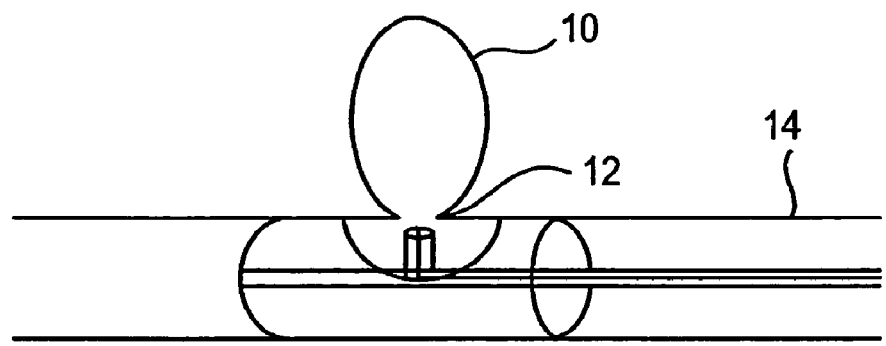
Figure 27:
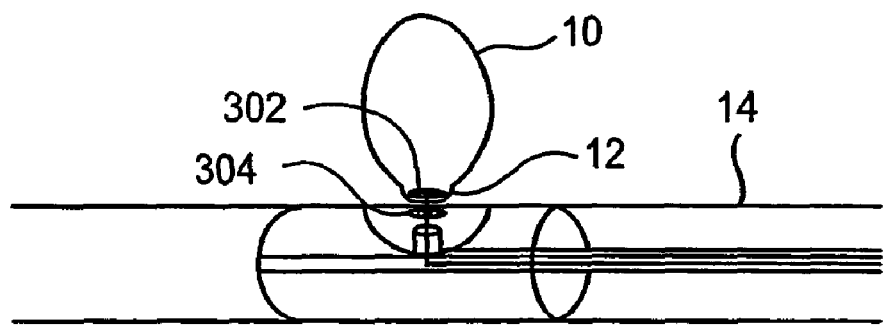
Figure 28:
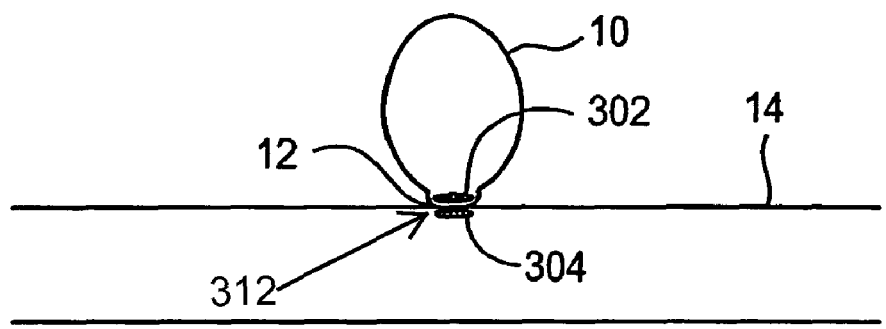

Turning now to FIG. 22, yet another embodiment of a clip in accordance with the present invention is illustrated. Clip 300 includes a longitudinally extending hollow, preferably cylindrical shaft (not illustrated) which contains a wire/bar/mandrel 308 to move the clip into an aneurysm. A pair of circular or oval self expanding frames 302, 304 are mounted on the end of the clip 300, and include a spring activated collapsing joint 306. See FIG. 27 and FIG. 28. As in other embodiments herein, radiopaque markers 310 are preferably provided on the frames to assist in positioning the clip 300 in the aneurysm neck 12. The diameter of the self expanding frames is broader than the diameter of the neck. See FIG. 25 through FIG. 28. The joint 306 includes at least one, and preferably a plurality (two are illustrated) leaf springs, as described above. The springs are oriented with both ends on one lateral side of the each of the frames, I.e., a first V-spring is mounted on the right side of the frames as illustrated in FIG. 22, and a second V-spring is mounted on the left side of the frames. Thus, when unconstrained by a carrying catheter, such as catheter 220, the frames tend to open up to the orientation illustrated in FIG. 22 and form a barrier 312. The clip is therefore self expanding. The frames support a lattice 309A and 309B. The alignment of the lattice cross structure 309A of the distal frame 302 can be offset from the alignment of the lattice cross structure 309B for the proximal frame 304. Hence when the frames are brought together by collapse of the joint 306, the combined frames form a barrier across the aneurysm neck. See FIG. 28.

Another aspect of the present invention includes methods of treating an aneurysm. Several embodiments of methods in accordance with the present invention will now be described with reference to several of the drawing figures, and with reference to several of the exemplary devices described herein. The methods of the present invention are not restricted to the particular devices described herein, but may be performed using other devices which are employable into an aneurysm cavity and onto the outer surface of which the aneurysm wall can be collapsed. By way of example and not of limitation, vascular coils, such as those described in the numerous U.S. patents to Guglielmi et al (see, e.g., U.S. Pat. No. 6,083,220), can be used as a device in the methods of the present invention.

Figure 3:
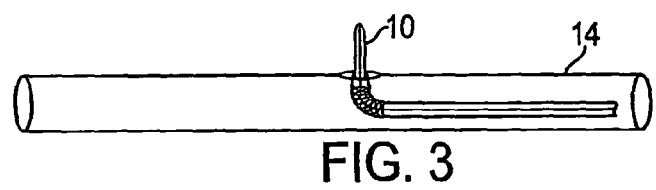
FIG. 3 illustrates a step later than that illustrated in FIG. 2 in the exemplary method.
Figure 4A:
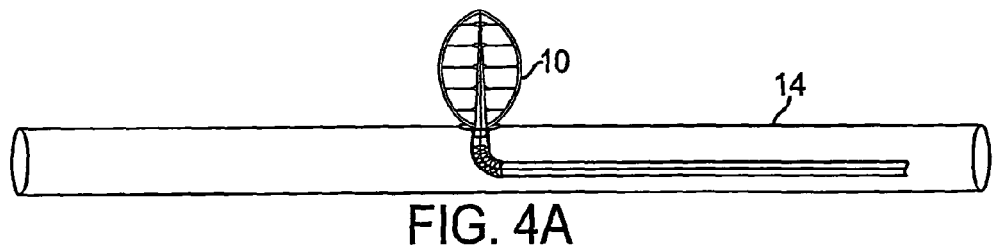
FIGS. 4a and 4b illustrate a step later than that illustrated in FIG. 2 in the exemplary method, utilizing two embodiments of apparatus illustrated in FIG. 1.
Figure 4B:
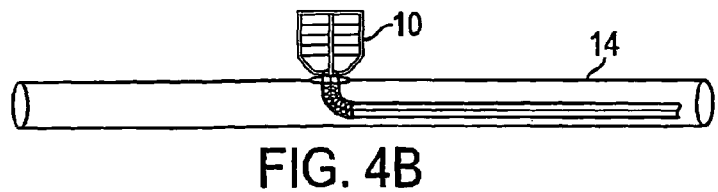

A first exemplary embodiment of a method in accordance with the present invention, given by way of example and not of limitation, includes, but is not limited to, the steps of:

1. Perform a road-mapping arteriogram with measurement of the three dimensional size of an aneurysm 10 and its neck 12 within the small and tortuous neurovascular systems.
2. Access the aneurysm neck using a steerable catheter, e.g. catheter 102.
3. Lock the distal end of the catheter in a position perpendicular to the center of the neck transverse axis.
4. Slowly inflate a balloon mounted on the distal end of the catheter with a diluted contrast medium up to the previously measured size of the neck (see FIG. 2).
5. Verify complete occlusion of the neck 12 by injection of contrast agent through side holes in the catheter positioned just proximal to the balloon, and simultaneously applying suction through a one-way valve at the distal end of the catheter. When no inflow of the contrast into the catheter is demonstrated together with deformation of the aneurysm with the suction, the aneurysm neck is completely closed.
6. With the neck completely closed, continue suction to almost complete collapse of the aneurysm by creating a vacuum within the aneurysm (see FIG. 3).
7. Obtain transverse and longitudinal measurement of the aneurysm, e.g. using MRI, CT scan, or the like.
8. Advance a compressed clip, the size of which has been chosen according to the previous measurements, through the distal end of the catheter. The clip, which is constructed using a principal similar to a self-expanding vascular stent, will start to expand as it is advanced into the aneurysm. The transverse axis of the clip is preferably maintained parallel to the longitudinal axis of the artery 14 from which the aneurysm 10 is arising (see FIGS. 4 and 5).
9. Maintain the vacuum within the aneurysm with continuous suction to ensure adherence of the aneurysm wall to the sides of the clip (FIG. 6a).
10. Begin proximal pulling of the wire or thread mounted within the stretching bar to telescope the very distal segment into the next proximal segment (see FIG. 6b).
11. The distal segment of the clip, which folds on itself if not stretched from both ends as described above, will start folding on itself together with the adjacent wall of the aneurysm as it becomes dislodged from the stretching bar (see FIG. 6c). The aneurysm wall is held to the outside of the clip by the suction.
12. By repeating the process described in steps 10 and 11, successive segments of the stretching bar and clip will continue to fold and complete collapse of the aneurysm will be achieved. (see FIG. 7) The catheter can then be withdrawn.

A second exemplary embodiment of a method in accordance with the present invention, given by way of example and not of limitation, includes, but is not limited to, the steps of:

1. Perform a road-mapping arteriogram.
2. Obtain measurements of the aneurysm, the neck of the aneurysm, and the parent artery.
3. Using a transvascular approach, e.g., a right femoral approach, position the balloon catheter 200 in the parent artery (using the guidance of the radiopaque markers on the periphery of the central working channel) with the distal segment of the balloon distal, e.g., immediately distal, of the aneurysm neck, and the proximal segment proximal, e.g., immediately proximal, to the aneurysm neck (see FIGS. 9-11).
4. Slowly inflate the balloon to achieve occlusion of the parent artery both proximal and distal to the neck.
5. Pull the steering thread within the catheter shaft to direct the steerable section of the catheter to a position as close and as perpendicular as possible to the neck (see FIG. 12).
6. Apply a moderate amount of suction using a suitable device, e.g., a syringe attached to a lock mounted on the proximal end of the catheter to decompress the aneurysm; activate the lock to maintain the relative vacuum in the aneurysm (see FIG. 10).
7. Stiffen the distal segment of the aneurysm clip with the stiffening wire by pulling on the proximal segment of the wire and then push it until it reaches the sealed top of the clip.
8. Push both the stiffening wire and the clip into the aneurysm cavity, firmly holding both of these elements together; the self-expanding frame of the clip will start to expand as the clip is deployed (see FIG. 13).
9. Apply strong suction through the catheter to collapse the aneurysm wall completely around the expanded clip (see FIG. 14).
10. Turn off the vacuum lock at the proximal end of the catheter while applying strong vacuum to the catheter lumen to ensure that a vacuum is maintained within the aneurysm to assist, and preferably ensure, that the aneurysm wall adheres to the outside of the clip.
11. Start pulling the stiffening wire through the sealed proximal end of the catheter to release the most distal segment of the clip, which will fold onto itself about the joint because of the action of the springs in the joints, together with the adjacent aneurysm wall which is held by the vacuum (see FIGS. 15, 16), which may be at least in part assisted by the force of the vacuum pushing inward on the frames of the clip.
12. Repeat steps 10 and 11 so that successive segments or sections of the clip continue to fold and at least partial, and preferably complete, collapse of the aneurysm will be achieved (see FIG. 17).
13. Rotate the shaft, e.g., counterclockwise, to dislodge the shaft from the collapsed segment(s) of the clip.

A third exemplary embodiment of a method in accordance with the present invention, given by way of example and not of limitation, includes, but is not limited to, the steps of the above described second embodiment, with the following modification. The clip is positioned at the neck of the aneurysm and the very proximal end of the aneurysm segment. Only the portion of the clip that is in the aneurysm is folded, leaving the rest of the aneurysm decompressed but not fully collapsed onto the outer surface of the clip (see FIGS. 18-21). This and other aspects of the invention can be particular useful in the treatment of aneurysms which include adhesions, which make complete collapse of the aneurysm wall difficult because they make the wall less pliable.

Figure 25:
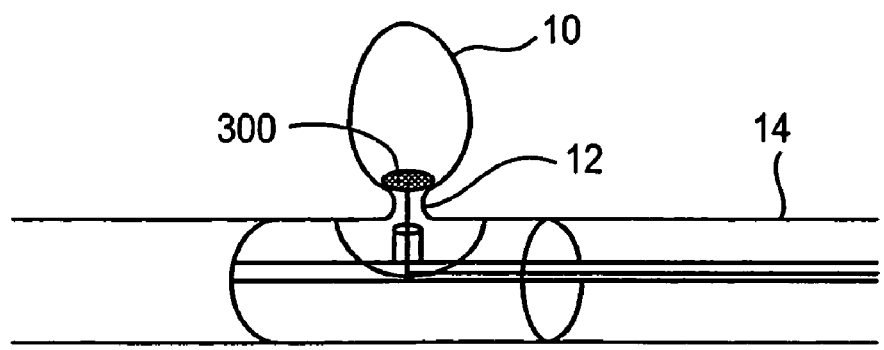
Figure 26:
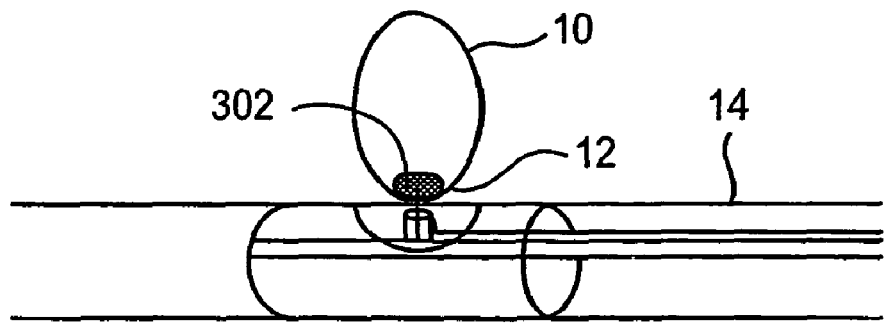

A fourth exemplary embodiment of a method in accordance with the present invention, given by way of example and not of limitation, includes, but is not limited to, utilizing the clip 300 (see FIG. 22) in the following manner and including the steps of:

1. Perform steps 1-6 as described in the second embodiment above.
2. Introduce the distal segment of the clip 300 to a point just distal of the neck of the aneurysm 10, i.e., just inside the aneurysm cavity (see FIG. 25). FIG. 25 shows the diameter of the expanded distal segment of the clip to be larger than the diameter of the aneurysm neck 12.
3. Apply strong suction and lock it in to maintain vacuum in the aneurysm cavity.

4. Pull the distal segment 302 of the clip to push (fold) down the aneurysm neck 12 (see FIG. 26).
5. Introduce the proximal segment 304 of the clip into the parent artery 14, e.g., through a catheter 220, just proximal of the neck and permit or cause the joint of the proximal segment to collapse thereby compressing the neck (see FIG. 27).
6. Dislodge the pushing wire by turning it, e.g., in a counterclockwise direction (see FIG. 28). The double frame of the proximal and distal clip occludes the flow of blood into the aneurysm. The double frame comprises a barrier 312 to an aneurysm created by the self expanding distal and proximal segments installed and forming a barrier across the aneurysm neck. The combined effect of the proximal and distal frame of the clip is to form a permanent barrier across the neck of the aneurysm to impede or obstruct the blood flow to the inside sac of the aneurysm leading to thrombosis and occlusion of the aneurysm. Also the lattice of the frame acts as a scaffolding for the lining of the vessel to grow causing permanent sealing of the aneurysm.

As will be readily appreciated by one of skill in the, the present invention also extends to the combination of a deployment catheter, such as catheter 220, with any of the embodiments of the aneurysm clips described herein to access and treat an aneurysm.

While the invention has been described in detail with reference to preferred embodiments thereof, it will be apparent to one skilled in the art that various changes can be made, and equivalents employed, without departing from the scope of the invention. Each of the aforementioned published documents is incorporated by reference herein in its entirety.

The invention claimed is:

1. A device for treating an aneurysm comprising:
    a clip configured to be folded within a catheter, said clip comprises
        a distal clip segment;
        a proximal clip segment; wherein each of said segments comprising a lattice, said lattice comprises a plurality of intersecting strands forming a plurality of openings;
        a collapsible joint, wherein a portion of said distal clip segment and a portion of said proximal clip segment are connected to said collapsible joint;
        wherein said distal and proximal clip segments are configured to expand when said respective clip segment becomes unconstrained by the catheter and wherein said expanded clip segments are configured to extend across a neck of an aneurysm in an expanded configuration; and wherein the lattice of the distal clip segment is offset from the lattice of the proximal clip segment when the distal and proximal segments are in the expanded configuration.

2. The device of claim 1 wherein said collapsible joint comprises at least one leaf spring configured to assist the proximal and distal clip segments expand when unconstrained by the catheter.

3. The device of claim 2 wherein said collapsible joint is configured to assist said clip segments expand by pulling one clip segment toward the other clip segment.

4. The device of claim 2 wherein said leaf spring comprises a first end and a second end, said first end attached to a portion of said distal clip segment and said second end attached to a portion of said proximal clip segment.

5. The device of claim 1 wherein at least one of said clip segments further comprises a frame circumscribing the lattice.

6. The device of claim 5 further comprising at least one radiopaque marker.

7. The device of claim 6 wherein said at least one radiopaque marker is located on said frame circumscribing the lattice.

8. The device of claim 1 wherein at least one of said distal and proximal clip segments comprises a circular or oval shape in the expanded configuration.

9. The device of claim 1 wherein the diameter of at least one of said clip segments is configured to be greater than the diameter of the neck of the aneurysm.

10. The device of claim 1 wherein both clip segments are configured to form a barrier across the neck of the aneurysm when said clip segments are expanded and extended across the neck of said aneurysm.

11. The device of claim 1 wherein said collapsible joint is configured to be releasably attached to a delivery wire.

12. A method for treating an aneurysm comprising the steps of:
    delivering a clip to an aneurysm with a catheter, wherein at least a portion of said clip is longitudinally folded within said catheter, said clip comprising a distal clip segment and a proximal clip segment connected by a collapsible spring joint;
    inserting said distal clip segment into said aneurysm by pushing said clip in the direction of the aneurysm, wherein said distal clip segment expands when unconstrained from said catheter;
    placing said distal clip segment adjacent a portion of a neck of said aneurysm, said distal clip segment extends across the neck of said aneurysm when expanded;
    forming a barrier across the neck of said aneurysm by releasing said proximal clip segment from said catheter, wherein said proximal clip segment expands when unconstrained from said catheter to extend across the neck of the aneurysm and attach said clip to a portion of said aneurysm,
    wherein a lattice of the distal clip segment is offset from a lattice of the proximal clip segment when the distal and proximal segments are in an expanded configuration.

13. The method of claim 12 wherein said catheter comprises a balloon catheter and further comprising the steps of:
    positioning said balloon catheter in a parent artery of said aneurysm, and
    inflating a balloon of said balloon catheter to achieve at least partial occlusion of said parent artery.

14. The method of claim 12 further comprising the steps of:
    applying suction sufficient to decompress the aneurysm; and
    activating a lock mechanism to maintain relative vacuum in the aneurysm.

* * * * *